United States Patent [19]

Suzuki et al.

[11] Patent Number: 4,736,049

[45] Date of Patent: Apr. 5, 1988

[54] ADDITION REACTION METHOD

[75] Inventors: Masahiko Suzuki; Takeshi Imai, both of Chiba, Japan

[73] Assignee: Toray Silicone Co. Ltd., Tokyo, Japan

[21] Appl. No.: 101,050

[22] Filed: Sep. 25, 1987

[30] Foreign Application Priority Data

Oct. 6, 1986 [JP] Japan .................... 61-237591

[51] Int. Cl.$^4$ ................................ C07F 7/08
[52] U.S. Cl. ...................... 556/479; 556/445; 556/453
[58] Field of Search .............. 556/479, 445, 453

[56] References Cited

U.S. PATENT DOCUMENTS

| 2,823,218 | 2/1958 | Speier et al. | 556/479 X |
| 3,057,902 | 10/1962 | Pike | 556/479 |
| 3,153,662 | 10/1964 | Pike | 556/479 |
| 3,925,434 | 12/1975 | Chuang | 556/479 X |
| 4,398,010 | 8/1983 | Adkins | 556/479 X |

Primary Examiner—Paul F. Shaver
Attorney, Agent, or Firm—Carl A. Yorimoto

[57] ABSTRACT

A process having the characteristic that a silicon compound having at least one hydrogen atom directly bonded to silicon in each molecule is addition reacted with an organic compound having at least one aliphatic double bond in each molecule in the presence of a platinum catalyst and an amide compound with the formula, $RCONR^1R^2$. The presence of the amide maximizes the yield of the desired beta-adduct and minimizes the yield of the alpha-adduct.

13 Claims, No Drawings

ADDITION REACTION METHOD

BACKGROUND OF THE INVENTION

The present invention relates to a method for conducting the addition reaction between silicon compounds having hydrogen directly bonded to organosilicon and organic compounds having aliphatic double bonds.

With regard to the reactions between SiH-containing silicon compounds and organic compounds having aliphatic double bonds, the addition reaction in the presence of a platinum catalyst, such as chloroplatinic acid, is known, for example, as described in *Journal of the American Chemical Society*, page 3601 (1960). However, the aforesaid addition-reaction method over chloroplatinic acid suffers from the problem of isomerization due to migration of the aliphatic double bond and consequently from the production of substantial quantities of the beta-adduct by-product in addition to the alpha-adduct target. For example, in the addition reaction between trichlorosilane and allyl chloride, 2-trichlorosilylchloropropane by-product is produced in addition to the 3-chloropropyltrichlorosilane target.

SUMMARY OF THE INVENTION

The object of the present invention is to eliminate this problem by providing a method for conducting the addition reaction between the silicon compound and an aliphatic double bond-containing organic compound in which little by-product is generated. The aforesaid object can be accomplished by means of an addition-reaction method which has the characteristic that a silicon compound having at least one hydrogen atom directly bonded to silicon in each molecule is addition reacted with an organic compound having at least 1 aliphatic double bond in each molecule in the presence of a platinum catalyst and an amide compound with the formula, $$RCONR^1R^2.$$

In the present invention, because the addition reaction between a silicon compound having at least 1 silicon-bonded hydrogen atom in each molecule and an organic compound having at least 1 aliphatic double bond in each molecule is carried out in the presence of platinum catalyst and an amide compound, the invention is characterized by the generation of only small quantities of by-product while having a high catalytic efficiency, and thus has high industrial utility.

DESCRIPTION OF THE INVENTION

In accordance with the instant invention, there is provided a process for the addition reaction of a hydrogen-containing silicon compound with an organic compound having at least one double bond under conditions that will be delineated herein. What is described therefore, is a process for minimizing the generation of by-products from the addition reaction of a hydrogen-containing silicon compound with an organic compound having at least one double bond, said process comprising reacting a silicon compound having at least one hydrogen atom directly bonded to silicon in each molecule with an organic compound having at least 1 aliphatic double bond in each molecule in the presence of a platinum catalyst and an amide compound with the formula, $$RCONR^1R^2,$$

wherein
R is a monovalent hydrocarbon group; and each $R^1$ and each $R^2$ are independently selected and are a hydrogen atom or a monovalent hydrocarbon group.

In explanation of the preceding, any silicon compound having at least one hydrogen atom directly bonded to silicon in each molecule is operative as the silicon compound in the present invention. Typical examples are monoorganosilanes, diorganosilanes, and triorganosilanes with the formulae, $$R^3{}_a SiH_{4-a},$$

or $$R^3{}_c SiH_d X_{4-c-d},$$

or $$R^3{}_e H_f SiO_{(4-e-f)/2},$$

wherein
$R^3$ is a monovalent hydrocarbon group: each X is independently selected and is selected from a group consisting of halogen atoms, alkoxy groups, and acyloxy groups; a has a value of 1, 2, or 3; c has a value of 0, 1, 2 or 3; d has a value of 1 or 2; (c+d) equals 1, 2, or 3; and f each has a value greater than 0 but less than 3; and (e+f) has a value greater than 1.8 but less than 2.2.

$R^3$ in the above formulae is a monovalent hydrocarbon group, and is exemplified by alkyl groups such as methyl, ethyl, propyl, and octyl; alkenyl groups such as vinyl, allyl, and propenyl; substituted alkyl groups such as 2-phenylethyl, 2-phenylpropyl, and 3,3,3-trifluoropropyl; aryl groups such as phenyl and tolyl; and substituted aryl groups. X is a halogen atom, for example, the chlorine, bromine, or iodine atom; or is an alkoxy group such as methoxy, ethoxy, propoxy, or methoxyethoxy; or is an acyloxy group such as acetoxy.

Specific examples of the aforementioned silanes having the formula $$R^3{}_a SiH_{4-a}$$

are triethylsilane, dimethylethylsilane, dimethylvinylsilane, methylsilane, and phenylsilane.

Specific examples of the aforementioned silanes with the formula $$R^3{}_c SiH_d X_{4-c-d}$$

are trichlorosilane, methyldichlorosilane, dimethylchlorosilane, and chloromethylsilane.

Specific examples of the aforementioned organohydrogen siloxanes having the formula $$R^3{}_e (H)_f SiO_{(4-e-f)/2}$$

are 1,3,5,7-tetramethylcyclotetrasiloxane, trimethylsilyl-terminated methylhydrogenpolysiloxanes, and trimethylsilyl-terminated methylhydrogensiloxane-dimethylsiloxane copolymers.

Specific examples of organic compounds having at least 1 aliphatic double bond in each molecule which are operative in the present invention are olefinic hydrocarbons such as ethylene, propylene, 1-butene, isobutene, and 1-pentene; diene hydrocarbons such as butadiene and pentadiene; aromatic unsaturated hydrocarbons such as styrene; cyclic unsaturated hydrocarbons such as cyclohexene and cyclobutene; unsaturated ethers such as methyl vinyl ether, divinyl ether, and phenyl vinyl ether; unsaturated halides such as allyl chloride, methacryl chloride, and allyl bromide; and vinyl group-containing organopolysiloxanes such as dimethylvinylsilyl-terminated dimethylpolysiloxanes.

The platinum catalyst operative in the present invention is concretely exemplified by finely divided platinum, finely divided platinum adsorbed on a carbon powder support, chloroplatinic acid, alcohol-modified chloroplatinic acid, olefin complexes of chloroplatinic acid, chloroplatinic acid-vinylsiloxane coordination compounds, and platinum black.

The amide compounds with formula $$RCONR^1R^2$$

which are used in the present invention function to increase the catalytic effect in the addition reaction under platinum catalysis while suppressing the appearance of by-product. R in the above formula is a monovalent hydrocarbon group and is exemplified by alkyl groups such as methyl, ethyl, propyl, and octyl; alkenyl groups such as vinyl, allyl, and propenyl; substituted alkyl groups such as 2-phenylethyl, 2-phenylpropyl, and 3,3,3-trifluoro propyl; aryl groups such as phenyl and tolyl; and substituted aryl groups. $R^1$ and $R^2$ are hydrogen atoms or monovalent hydrocarbon groups, and said monovalent hydrocarbon groups are exemplified as above.

Said amide compound is specifically exemplified by N-methylacetamide. acetamide, propionamide, N-ethylacetamide, N,N-dimethylacetamide, and N-benzylacetamide.

While the method of the present invention consists of the addition reaction of a silicon compound as above with an aliphatic double bond-containing organic compound as above in the presence of a platinum catalyst and amide compound, the platinum catalyst and amide compound may be mixed in advance to afford a catalyst composition, or they may be added separately to the addition reaction. No specific restriction obtains on the use quantities of the silicon compound or aliphatic double bond-containing organic compound, but it is preferred that the molar ratio of aliphatic double bond-containing organic compound to silicon compound be 0.3 to 3.0. Nor is the use quantity of platinum catalyst specifically restricted, although it preferably falls within the range of $10^{-6}$ to $10^{-7}$ moles per 1 mole silicon-bonded hydrogen atoms. The amide compound is preferably used in the range of 1 to 10 moles per 1 mole platinum present in said platinum catalyst.

The reaction temperature will vary with the type of silicon compound, aliphatic double bond-containing organic compound, platinum catalyst, and amide compound, but is generally preferably in the range of 20° C. to 200° C.

The atmosphere in the addition-reaction system is also not specifically restricted, and may be air or an inert gas, at ambient pressure or at elevated pressures. The simultaneous use is also permissible of a solvent such as an aromatic hydrocarbon solvent (benzene, toluene, xylene, etc.), a ketone solvent, chlorinated hydrocarbon solvent, organosilane, organopolysiloxane, etc.

So that those skilled in the art may better appreciate or understand the instant invention, the following examples are presented. These examples are meant to be illustrative and are not to be construed as limiting the claims delineated herein.

EXAMPLE 1

A catalyst solution was prepared by thoroughly mixing 50 g of a 2 weight percent (wt %) isopropanolic solution of chloroplatinic acid hexahydrate with 0.17 g N,N-dimethylacetamide. 40 g of 3-chloropropylmethyldichlorosilane as solvent and 0.07 g of the previously prepared catalyst solution were placed in a 300 ml four-neck flask equipped with condenser, stirrer, thermometer, and addition funnel. The internal temperature of the flask was brought to 60° C., and a mixture of 41.2 g allyl chloride and 62.0 g methyldichlorosilane was gradually dripped in. The evolution of heat due to the addition reaction between the allyl chloride and methyldichlorosilane was observed during addition.

The composition of the reaction product was analyzed by gas chromatography, and the results showed that 3-chloropropylmethyldichlorosilane had been produced in a yield of 79 mole percent (mole %) based on the allyl chloride added.

COMPARISON EXAMPLE 1

(not within the scope of the instant invention)

An addition reaction was conducted exactly as described in Example 1 with the exception that 0.07 g of a 2 wt % isopropanolic chloroplatinic acid hexahydrate solution was used as the catalyst solution. The result was the production of 3-chloropropylmethyldichlorosilane in a yield of 59.4 mol %. The temperature gradually fell off during addition, and external heating was necessary in order to maintain the temperature at the specified value.

EXAMPLE 2

A catalyst solution was prepared by thoroughly mixing 50 g of a 2 wt % isopropanolic chloroplatinic acid hexahydrate solution with 0.17 g N,N-dimethylacetamide. 40 g 3-chloropropyltrichlorosilane as solvent and 0.07 g of previously prepared catalyst solution were placed in a 300 ml four-neck flask equipped with condenser, stirrer, thermometer, and addition funnel. The internal temperature of the flask was brought to 60° C., and a mixture of 38.7 g allyl chloride and 68.5 g trichlorosilane was gradually dripped in. The evolution of heat due to the addition reaction between the allyl chloride and trichlorosilane was observed during addition.

When the composition of the reaction product was analyzed by gas chromatography, it was found that 3-chloropropyltrichlorosilane had been produced in a yield of 84.7 mol % based on the allyl chloride taken.

COMPARISON EXAMPLE 2

(not within the scope of the instant invention)

An addition reaction was conducted exactly as described in Example 2 with the exception that 0.07 g of 2 wt % isopropanolic chloroplatinic acid hexahydrate was used as the catalyst solution.

The result was the production of 3-chloropropyltrichlorosilane in a yield of 78.3 mol %. The temperature gradually fell off during addition, and external heating was necessary in order to maintain the temperature at the specified value.

EXAMPLE 3

A catalyst solution was prepared by thoroughly mixing 50 g of a 2 wt % isopropanolic chloroplatinic acid hexahydrate solution with 0.17 g N,N-dimethylacetamide. 105.6 g styrene and 0.16 g of previously prepared catalyst solution were placed in a 500 ml four-neck flask equipped with condenser, stirrer, thermometer, and addition funnel. The internal temperature of the flask was brought to 90° C., and 127.3 g methyldichlorosilane was gradually dripped in to conduct the addition reaction.

When the composition of the reaction product was analyzed by gas chromatography, a composition of 90% beta-methyldichlorosilylethylbenzene and 10% alpha-methyldichlorosilylethylbenzene was found.

COMPARISON EXAMPLE 3

(not within the scope of the instant invention)

An addition reaction was conducted exactly as described in Example 3 with the exception that 0.16 g of a 2 wt % isopropanolic chloroplatinic acid hexahydrate solution was used as the catalyst solution.

The composition of the reaction product was analyzed by gas chromatography, and a composition of 60% beta-methyldichlorosilylethylbenzene and 40% alpha-methyldichlorosilylethylbenzene was found.

What is claimed is:

1. A process for minimizing the generation of by-products from the addition reaction of a hydrogen-containing silicon compound with an organic compound having at least one double bond, said process comprising reacting a silicon compound having at least one hydrogen atom directly bonded to silicon in each molecule with an organic compound having at least 1 aliphatic double bond in each molecule in the presence of a platinum catalyst and an amide compound with the formula, $$RCONR^1R^2,$$

wherein

R is a monovalent hydrocarbon group; and each $R^1$ and each $R^2$ are independently selected and are a hydrogen atom or a monovalent hydrocarbon group.

2. A process according to claim 1, wherein the silicon compound having at least one hydrogen atom directly bonded to silicon has the formula, $$R^3{}_aSiH_{4-a},$$

or $$R^3{}_cSiH_dX_{4-c-d},$$

or $$R^3{}_eH_fSiO_{(4-e-f)/2},$$

wherein $R^3$ is a monovalent hydrocarbon group; each X is independently selected and is selected from a group consisting of halogen atoms, alkoxy groups, and acyloxy groups; a has a value of 1, 2, or 3; c has a value of 0, 1, 2 or 3; d has a value of 1 or 2; (c+d) must equal 1, 2, or 3; e and f each has a value greater than 0 but less than 3; and (e+f) has a value greater than 1.8 but less than 2.2.

3. A process according to claim 2, wherein $R^3$ is monovalent hydrocarbon group and is selected from a group consisting of alkyl groups, alkenyl groups, substituted alkyl groups, and substituted aryl groups.

4. A process according to claim 1, wherein the organic compound having at least one aliphatic double bond is selected from a group consisting of olefinic hydrocarbons, diene hydrocarbons, aromatic unsaturated hydrocarbons, unsaturated ethers, unsaturated halides, unsaturated ethers, and vinyl group-containing organopolysiloxanes.

5. A process according to claim 1, wherein the platinum catalyst is selected from a group consisting of platinum metal, platinum adsorbed on a solid support, chloroplatinic acid, alcohol-modified chloroplatinic acid, olefin complexes of chloroplatinic acid, chloroplatinic acid-vinylsiloxane coordination compounds, and platinum black.

6. A process according to claim 1, wherein the molar ratio of the organic compound having at least 1 aliphatic double bond in each molecule to the silicon compound having at least one hydrogen atom directly bonded to silicon in each molecule is in a range from about 0.3 to 3.

7. A process according to claim 1, wherein the amide compound is present at a concentration in the range of from about 1 to 10 moles per mole of platinum present in the platinum catalyst.

8. A process according to claim 1, wherein the silicon compound having at least one hydrogen atom directly bonded to silicon, the organic compound having at least 1 aliphatic double bond in each molecule, the platinum catalyst, and the amide compound are contacted at a temperature in the range of from about 20° C. to 200° C.

9. A process according to claim 1, wherein the silicon compound having at least one hydrogen atom directly bonded to silicon, the organic compound having at least 1 aliphatic double bond in each molecule, the platinum catalyst, and the amide compound are contacted in the presence of a solvent.

10. A process according to claim 9, wherein the solvent is selected from a group consisting of aromatic hydrocarbons, ketones, chlorinated hydrocarbons, organosilanes, and organopolysiloxanes.

11. A process according to claim 1, wherein the silicon compound having at least one hydrogen atom directly bonded to silicon in each molecule is methyldichlorosilane, wherein the organic compound having at least 1 aliphatic double bond in each molecule is allyl chloride, wherein the platinum catalyst is an alcoholic solution of chloroplatinic acid hexahydrate, and wherein the amide compound is N,N-dimethylacetamide.

12. A process according to claim 1, wherein the silicon compound having at least one hydrogen atom directly bonded to silicon in each molecule is trichlorosilane, wherein the organic compound having at least 1 aliphatic double bond in each molecule is allyl chloride, wherein the platinum catalyst is an alcoholic solution of chloroplatinic acid hexahydrate, and wherein the amide compound is N,N-dimethylacetamide.

13. A process according to claim 1, wherein the silicon compound having at least one hydrogen atom directly bonded to silicon in each molecule is methyldichlorosilane, wherein the organic compound having at least 1 aliphatic double bond in each molecule is styrene, wherein the platinum catalyst is an alcoholic solution of chloroplatinic acid hexahydrate, and wherein the amide compound is N,N-dimethylacetamide.

* * * * *